United States Patent
Grillo et al.

(10) Patent No.: US 10,563,165 B2
(45) Date of Patent: Feb. 18, 2020

(54) ORGANIC WASTE DIGESTER SYSTEM

(71) Applicant: BioGreen 360, Inc., Stratham, NH (US)

(72) Inventors: Paul Grillo, Exeter, NH (US); Bruce Secovich, Hudson, NH (US)

(73) Assignee: BioGreen 360, Inc., Stratham, NH (US)

( * ) Notice: Subject to any disclaimer, the term of this patent is extended or adjusted under 35 U.S.C. 154(b) by 0 days.

(21) Appl. No.: 15/501,595

(22) PCT Filed: May 29, 2015

(86) PCT No.: PCT/US2015/033212
§ 371 (c)(1),
(2) Date: Feb. 3, 2017

(87) PCT Pub. No.: WO2016/022198
PCT Pub. Date: Feb. 11, 2016

(65) Prior Publication Data
US 2017/0226466 A1    Aug. 10, 2017

Related U.S. Application Data

(60) Provisional application No. 62/033,437, filed on Aug. 5, 2014.

(51) Int. Cl.
C05F 11/08 (2006.01)
C05F 9/02 (2006.01)
(Continued)

(52) U.S. Cl.
CPC ............ *C12M 45/20* (2013.01); *A23K 20/10* (2016.05); *B02C 18/0084* (2013.01);
(Continued)

(58) Field of Classification Search
CPC . B02C 18/00; B02C 18/0084; B02C 18/0092; B02C 18/142; B02C 18/144; B02C 18/145; B02C 23/02; B09B 3/0083; C10L 5/445; C10L 2290/08; C10L 2290/24; C10L 2290/26; C10L 2290/36; C12M 45/02; C12M 45/03; Y02W 10/00; Y02W 10/10; Y02W 10/20; Y02W 30/00;
(Continued)

(56) References Cited

U.S. PATENT DOCUMENTS 3,233,976 A    8/1966    Varro et al.
3,556,286 A *  1/1971    Naito .................... B65G 21/22
                                                  198/823
(Continued)

FOREIGN PATENT DOCUMENTS

GB        2462651 A      2/2010
JP        10-165928 A    6/1998
WO        2012/009462 A2 1/2012

Primary Examiner — Shelley M Self
Assistant Examiner — Smith Oberto Bapthelus
(74) Attorney, Agent, or Firm — Verrill Dana, LLP

(57) ABSTRACT

An organic waste digester system is provided. The system includes a heated hopper unit within the housing to receive organic waste. An agitation mechanism mixes the organic waste along with a microbe mixture to aid breakdown of the waste. Liquefied organic waste is discharged through an outlet and conveyed to a drying unit downstream of the hopper unit. The drying unit includes a microwave dryer unit.

19 Claims, 18 Drawing Sheets

(51) Int. Cl.

| | |
|---|---|
| *C05F 17/02* | (2006.01) |
| *B09B 3/00* | (2006.01) |
| *A23K 20/10* | (2016.01) |
| *B02C 23/02* | (2006.01) |
| *C12M 1/00* | (2006.01) |
| *C05F 17/00* | (2020.01) |
| *B02C 18/00* | (2006.01) |
| *C10L 5/44* | (2006.01) |
| *C12M 1/33* | (2006.01) |

(52) U.S. Cl.
CPC ............... *B02C 23/02* (2013.01); *B09B 3/00* (2013.01); *B09B 3/0083* (2013.01); *C05F 9/02* (2013.01); *C05F 11/08* (2013.01); *C05F 17/0063* (2013.01); *C05F 17/02* (2013.01); *C10L 5/445* (2013.01); *C12M 45/02* (2013.01); *C12M 45/03* (2013.01); *C10L 2290/08* (2013.01); *C10L 2290/24* (2013.01); *C10L 2290/26* (2013.01); *C10L 2290/36* (2013.01); *Y02A 40/215* (2018.01); *Y02E 50/10* (2013.01); *Y02E 50/30* (2013.01); *Y02P 20/145* (2015.11); *Y02W 30/43* (2015.05)

(58) Field of Classification Search
CPC ..... Y02W 30/20; Y02W 30/40; Y02W 30/43; Y02W 30/521; Y02W 30/523; B65F 2210/00; B65F 2210/137; B65F 2210/168; B65F 2210/169; B65F 2210/182; C05F 3/00; C05F 3/04; C05F 3/06; C05F 7/00; C05F 9/00; C05F 9/02; C05F 9/04; C05F 17/00; C05F 17/0018; C05F 17/0027; C05F 17/0081; C02F 2301/10; C02F 3/00
USPC ...... 210/175, 601, 612, 613; 435/289–290.4, 435/262, 267; 198/818, 823, 824, 702
See application file for complete search history.

(56) References Cited

U.S. PATENT DOCUMENTS

| | | | |
|---|---|---|---|
| 3,590,202 A * | 6/1971 | Day | H05B 6/705 |
| | | | 219/681 |
| 3,872,603 A | 3/1975 | Williams et al. | |
| 4,035,598 A * | 7/1977 | Van Amsterdam | H01P 3/123 |
| | | | 219/690 |
| 5,337,964 A * | 8/1994 | Buehlmann | B03B 9/06 |
| | | | 241/17 |
| 5,353,998 A | 10/1994 | Sansing | |
| 5,393,961 A | 2/1995 | Umekage et al. | |
| 5,496,730 A * | 3/1996 | Teramachi | C05F 17/0027 |
| | | | 435/290.2 |
| 5,980,823 A * | 11/1999 | Nekozuka | A61L 11/00 |
| | | | 422/4 |
| 6,139,744 A * | 10/2000 | Spears | A47K 11/023 |
| | | | 210/614 |
| 6,224,646 B1 * | 5/2001 | Arato | C02F 3/28 |
| | | | 71/9 |
| 6,470,597 B1 | 10/2002 | Stipp | |
| 6,863,826 B2 | 3/2005 | Sheets | |
| 9,603,203 B2 * | 3/2017 | Wilber | H05B 6/701 |
| 2002/0030012 A1 | 3/2002 | Sullivan et al. | |
| 2003/0034232 A1* | 2/2003 | Kaeb | B65G 15/08 |
| | | | 198/819 |
| 2005/0092741 A1* | 5/2005 | Eves, II | A61L 2/12 |
| | | | 219/699 |
| 2006/0000108 A1* | 1/2006 | Cho | F26B 1/00 |
| | | | 34/259 |
| 2006/0049185 A1* | 3/2006 | Masson | H05B 6/782 |
| | | | 219/700 |
| 2009/0218196 A1* | 9/2009 | Gronvall | B29C 70/68 |
| | | | 198/497 |
| 2010/0058821 A1* | 3/2010 | Romano | C05F 17/0063 |
| | | | 71/11 |
| 2011/0179841 A1* | 7/2011 | Lu | C05F 7/00 |
| | | | 71/12 |
| 2012/0020844 A1 | 1/2012 | Foret | |
| 2013/0089918 A1 | 4/2013 | Atkinson | |
| 2013/0205649 A1* | 8/2013 | Larsen | C08J 11/16 |
| | | | 44/307 |

* cited by examiner

SECTION E-E

SECTION A-A

SECTION C-C

SECTION D-D

SECTION B-B

SECTION H-H

ORGANIC WASTE DIGESTER SYSTEM

CROSS-REFERENCE TO RELATED APPLICATIONS

This application claims the benefit under 35 U.S.C. § 119(e) of U.S. Provisional Patent Application No. 62/033,437, filed on Aug. 5, 2014, entitled "Organic Waste Digester System," the disclosure of which is incorporated by reference herein.

BACKGROUND

Organic waste is a large component of all waste generated by households, businesses and institutions.

SUMMARY OF THE INVENTION

An organic waste digester system is provided that reduces the volume of organic waste by 80-90%. The discharge product can be composted more rapidly than organic waste that has not been first digested. It also has application as an animal feed amendment as well as a fuel source. Also, if not subsequently utilized, the discharge product takes up much less volume in a landfill.

The organic waste digester system includes a housing and a control system. A hopper unit is located within the housing, having an opening to receive organic waste. An agitation mechanism mixes the organic waste, and a heater heats the organic waste in the hopper unit. A microbe mixture is added to aid in the breakdown of the organic waste. The liquefied organic waste is discharged through an outlet to a drying unit downstream of the hopper unit.

In one embodiment, the drying unit comprises a microwave drying unit including a microwave chamber and one or more magnetrons disposed to introduce microwave energy via one or more waveguides into the microwave chamber.

DESCRIPTION OF THE DRAWINGS

The invention will be more fully understood from the following detailed description taken in conjunction with the accompanying drawings in which.

DETAILED DESCRIPTION OF THE INVENTION

The disclosure of U.S. Provisional Patent Application No. 62/033,437, filed on Aug. 5, 2014, entitled "Organic Waste Digester System," is incorporated by reference herein.

An organic waste digester system is provided that can recycle organic waste including raw and cooked fish, meat and poultry, small bones, eggs and egg shells, fruits, vegetables, dairy products, and grain products. In a first stage, the organic waste is degraded and liquefied by heating and mixing. This process is accelerated by the addition of microbes. In a second stage, the liquefied waste is dried and dehydrated. The discharge product is 80-90% dry and reduced in mass by 80-90%. It is stable and can be stored for several months. This discharge product is a compostable material and can be sent to a compositing facility or to a landfill. The discharge product also has uses as an animal feed amendment or a fuel source.

Figure 1:
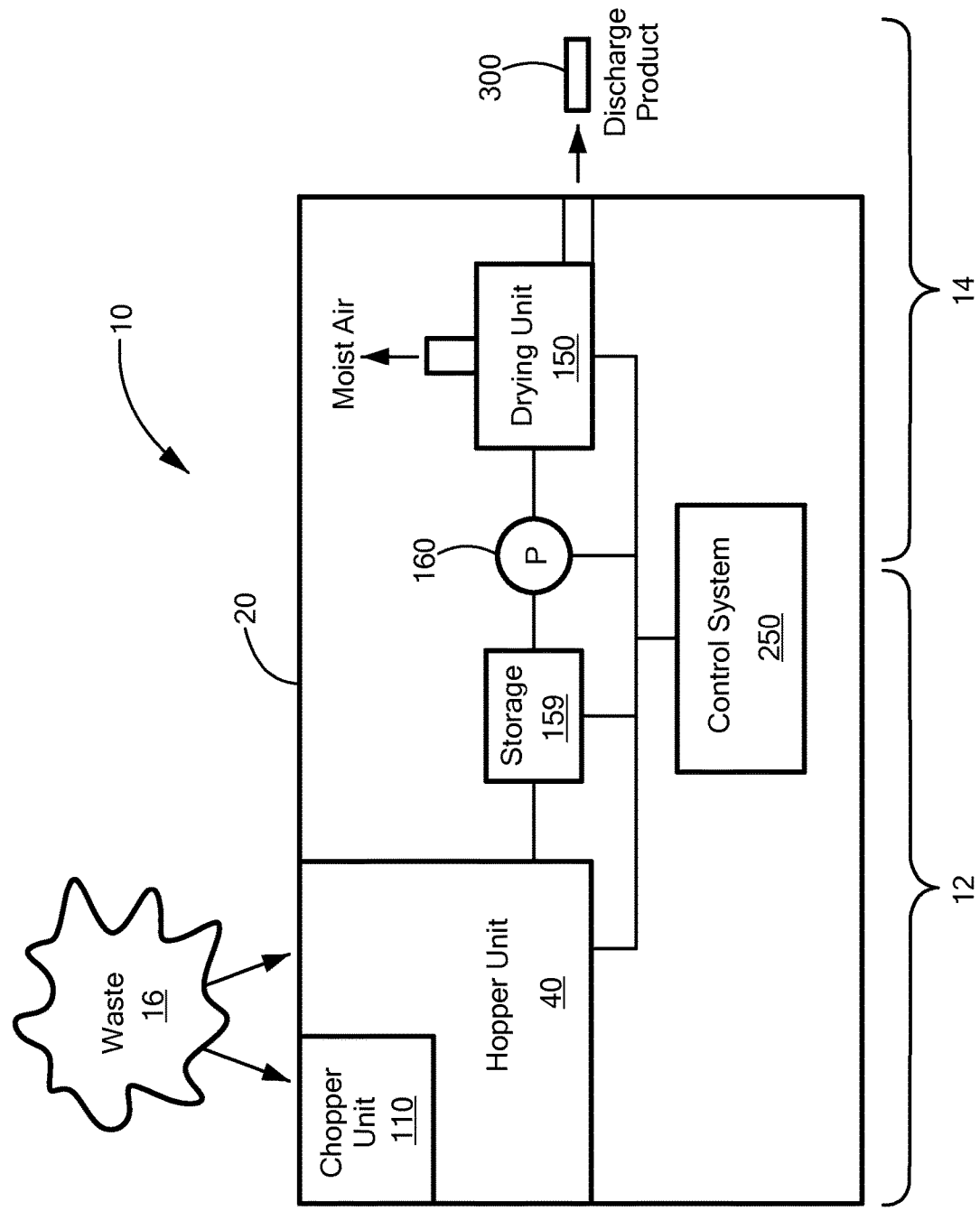
FIG. 1 is a schematic illustration of an organic waste digester system according to the present invention.
Figure 2:
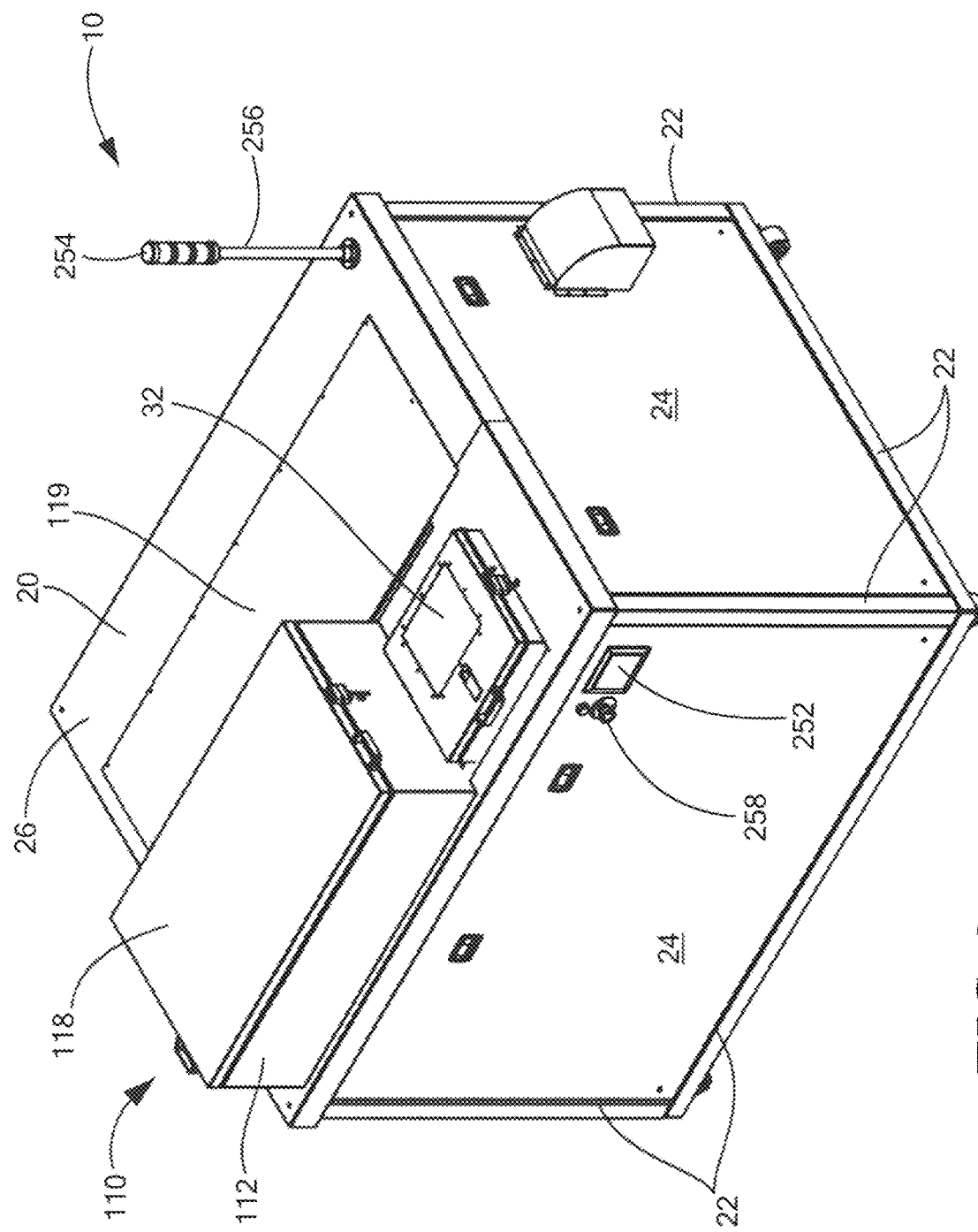
FIG. 2 is a front isometric view of one embodiment of an organic waste digester system.
Figure 3:
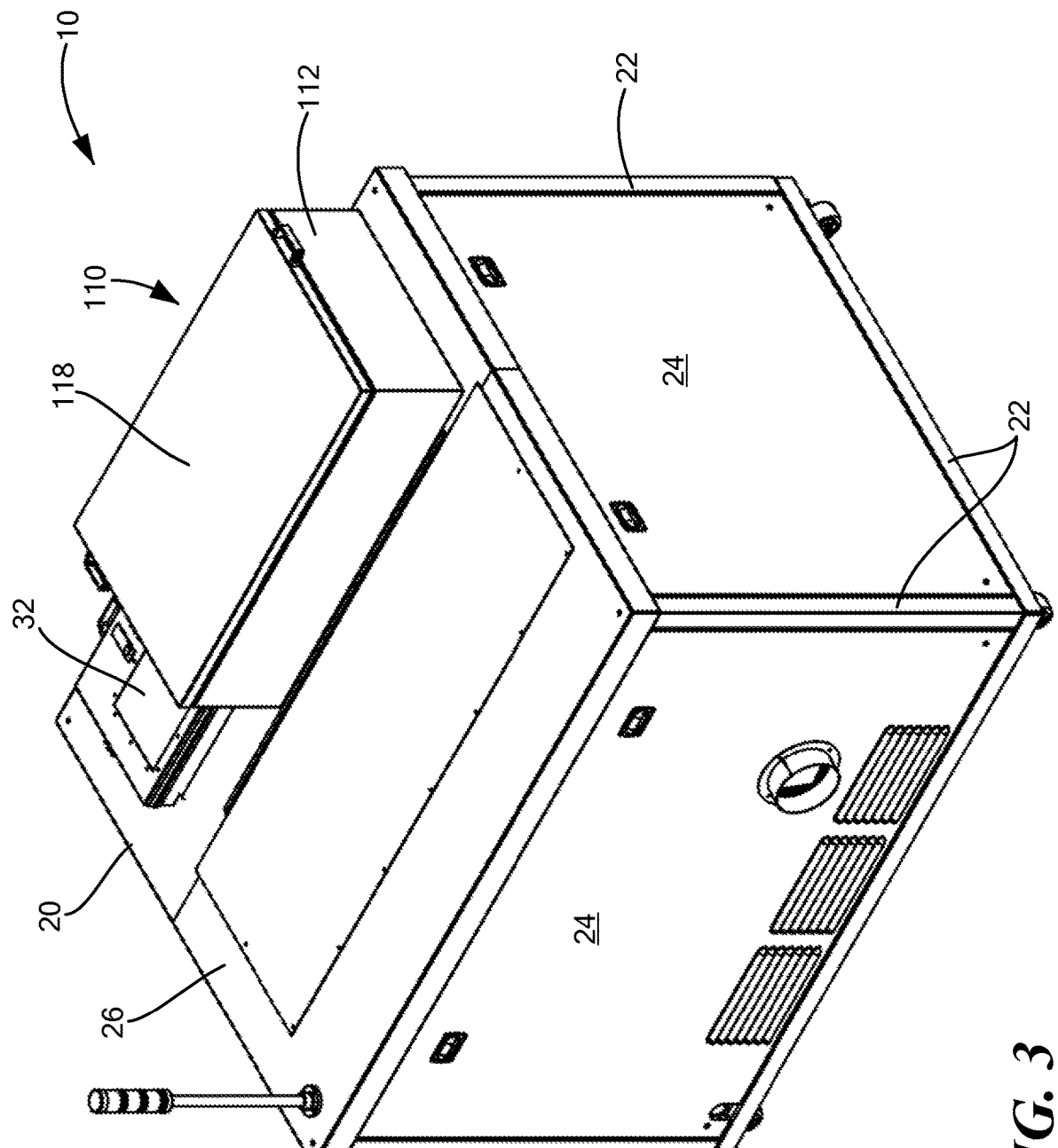
FIG. 3 is a rear isometric view of the organic waste digester system of FIG. 2.
Figure 4:
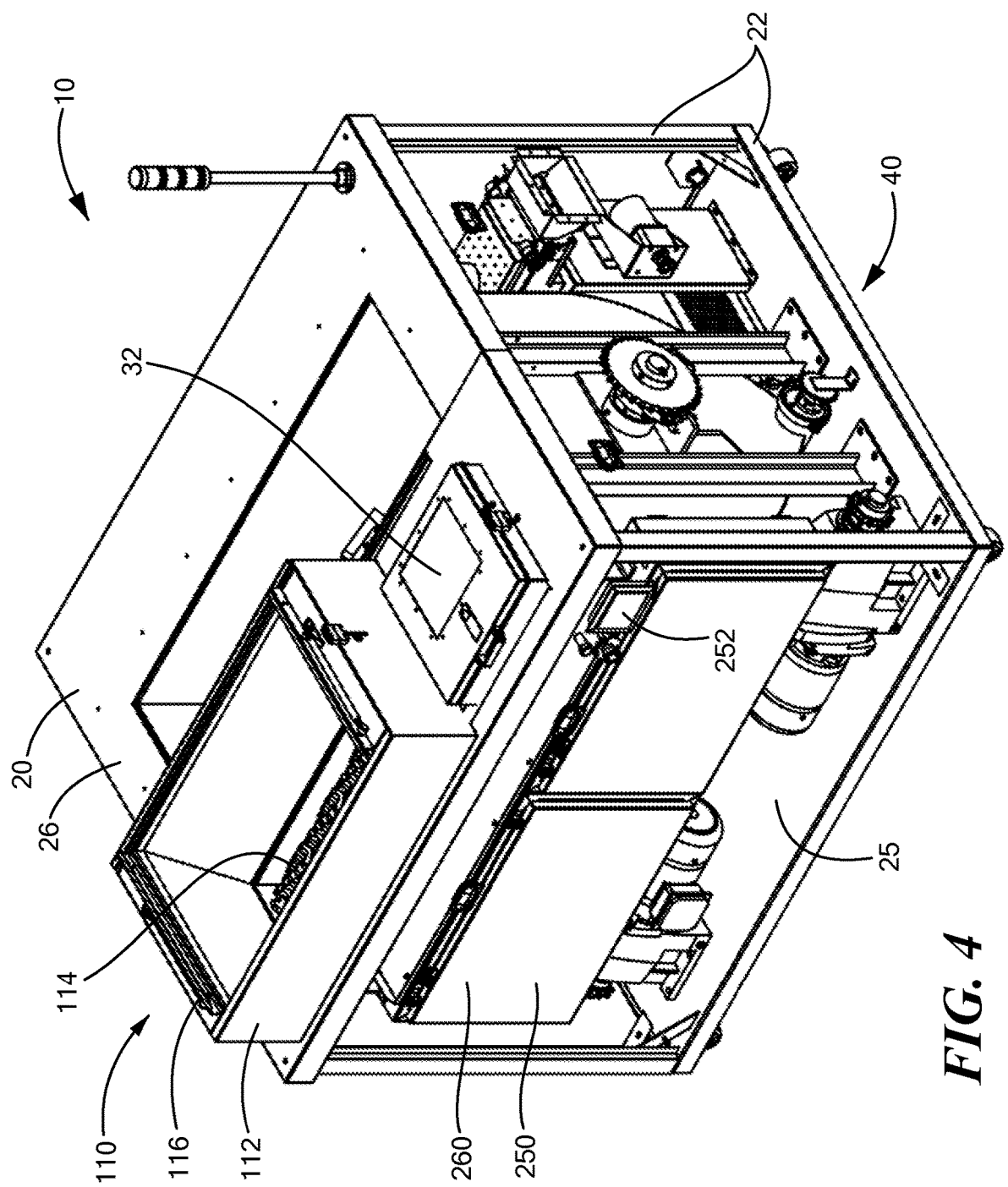
FIG. 4 is a front isometric view of the organic waste digester system of FIG. 2 with housing panels removed.
Figure 5:
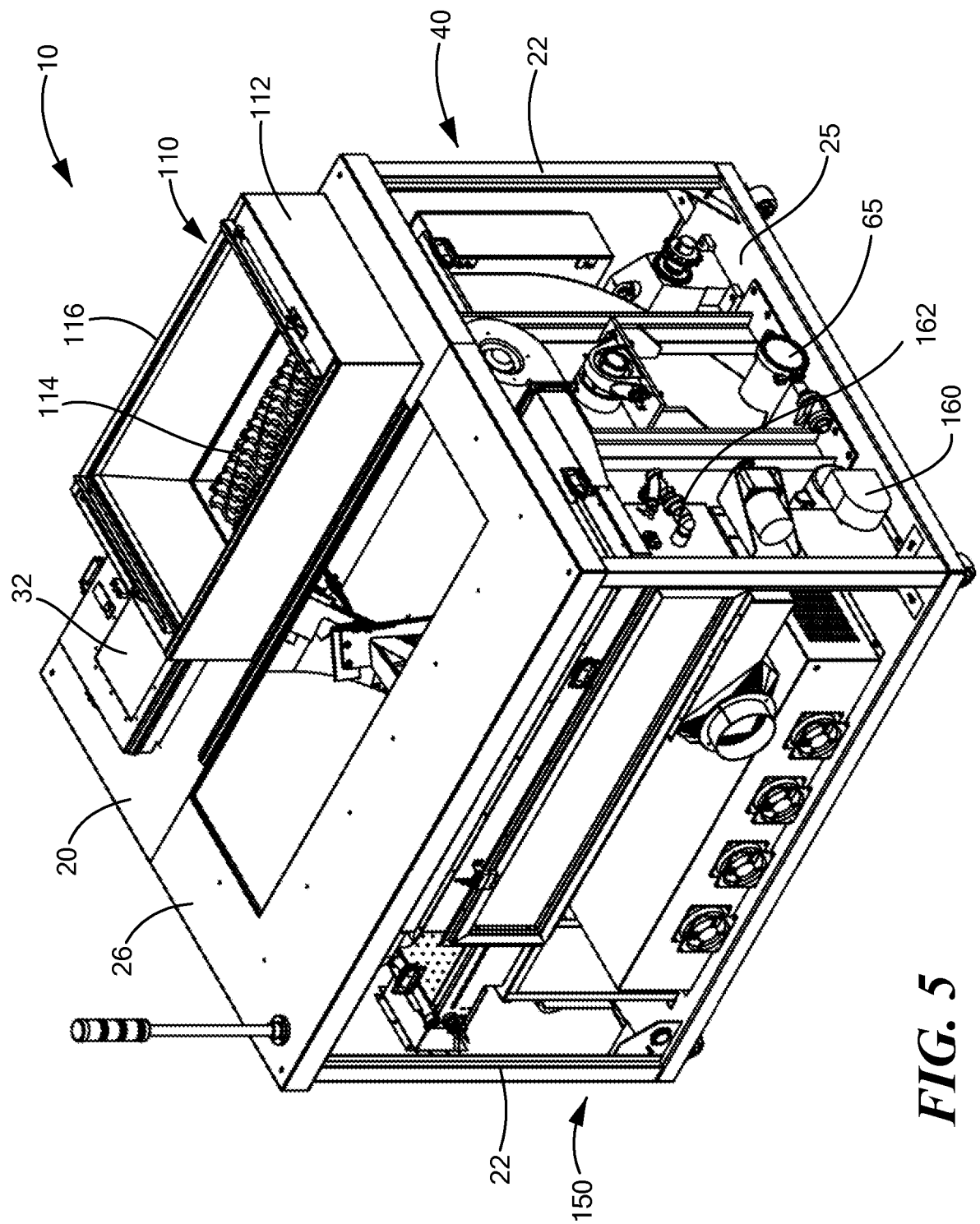
FIG. 5 is a rear isometric view of the organic waste digester system of FIG. 2 with housing panels removed.
Figure 6:
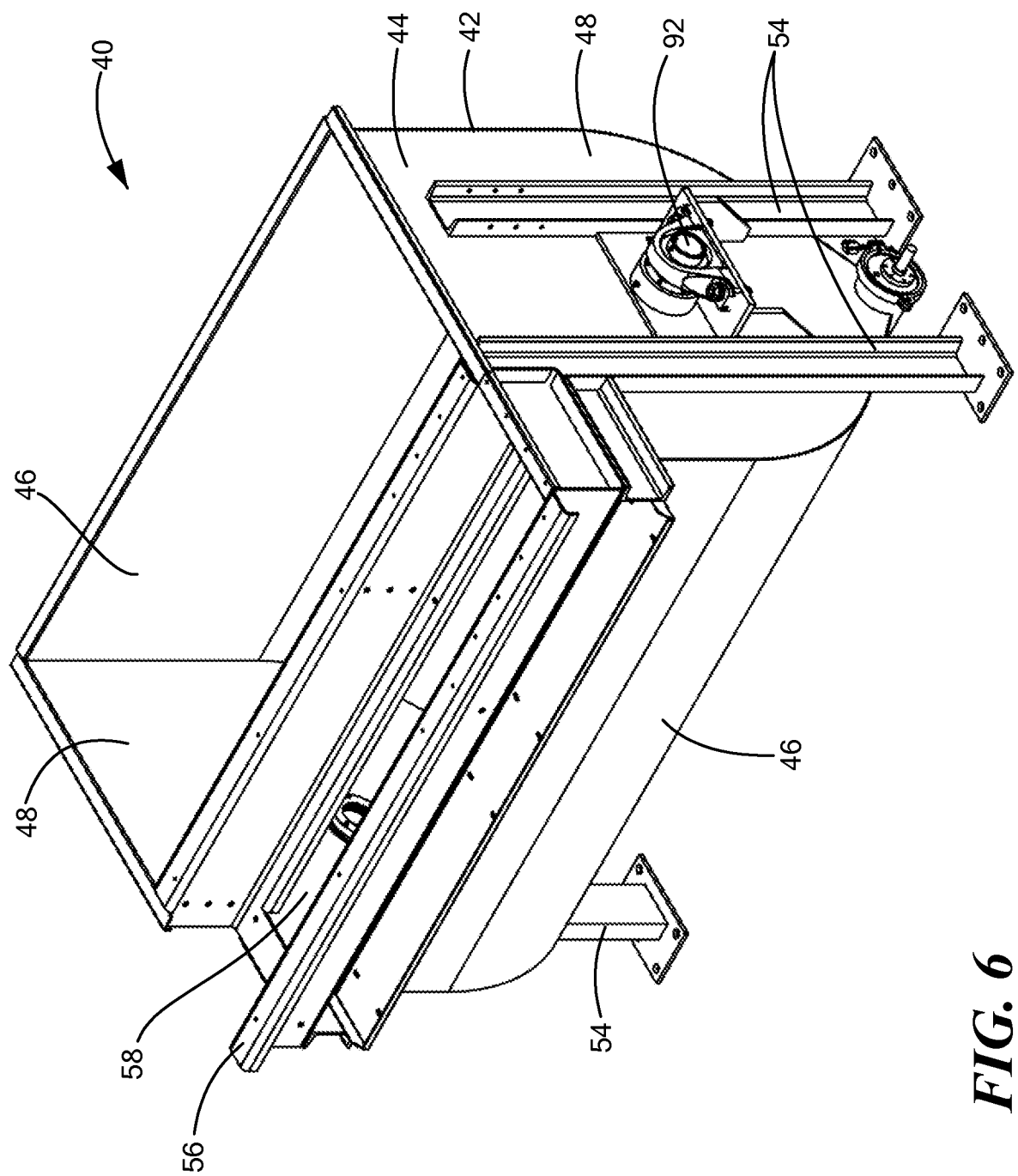
FIG. 6 is an isometric view of a hopper unit of the organic waste digester system of FIG. 2.
Figure 7:
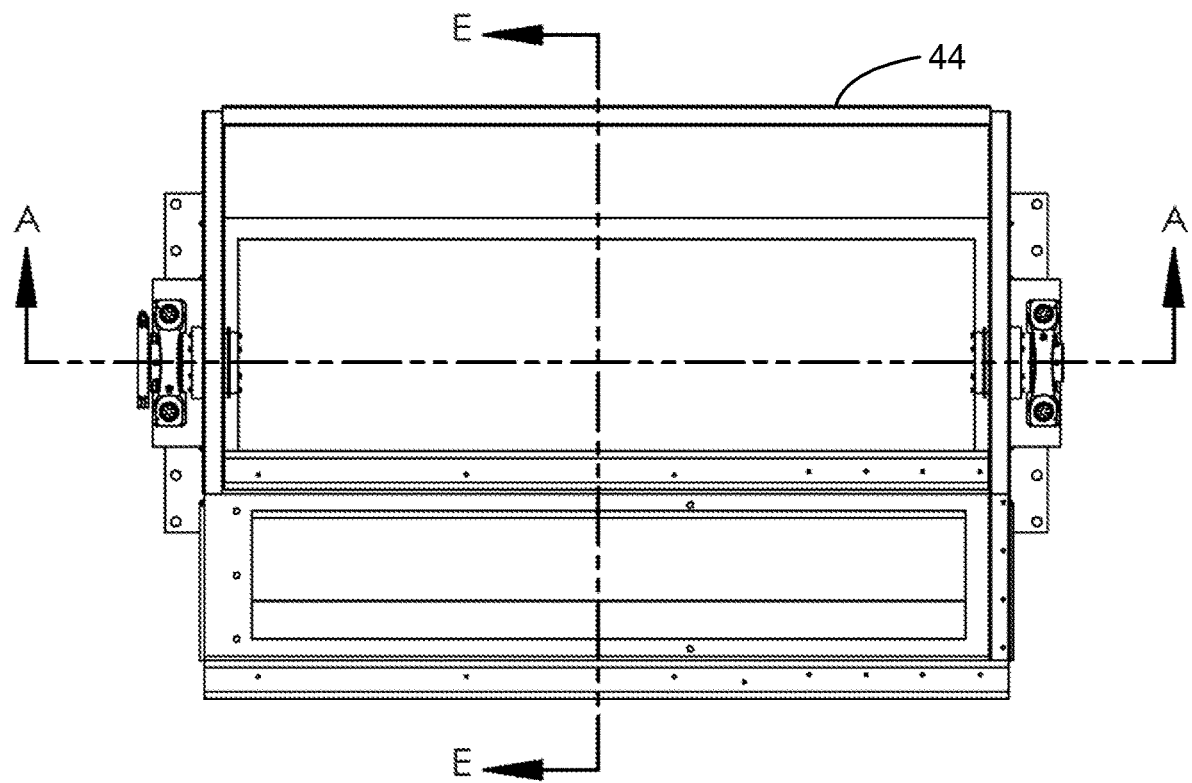
FIG. 7 is a top view of the hopper unit of FIG. 6.
Figure 8:
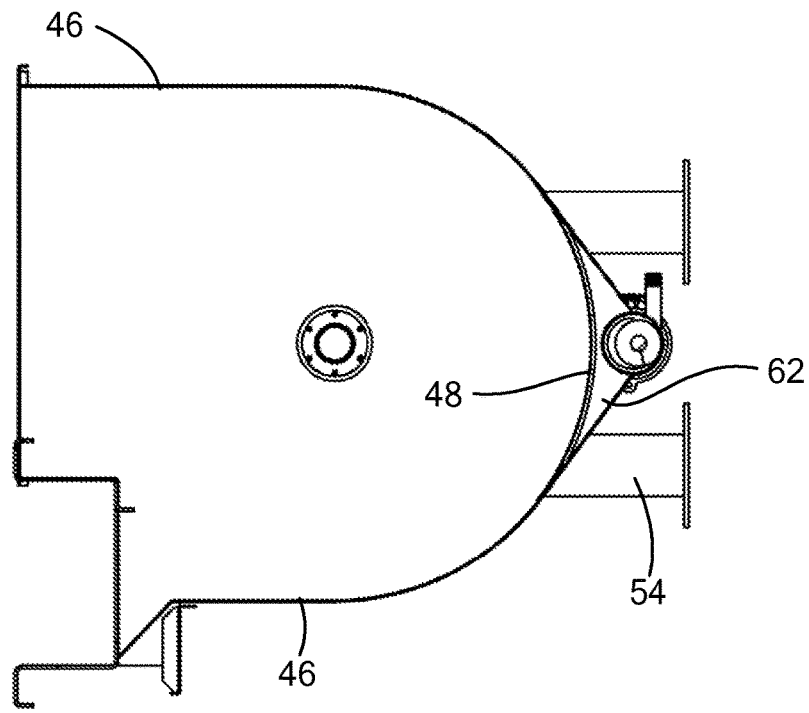
FIG. 8 is a cross-sectional side view of the hopper unit of FIG. 6 along line E-E of FIG. 7.
Figure 9:
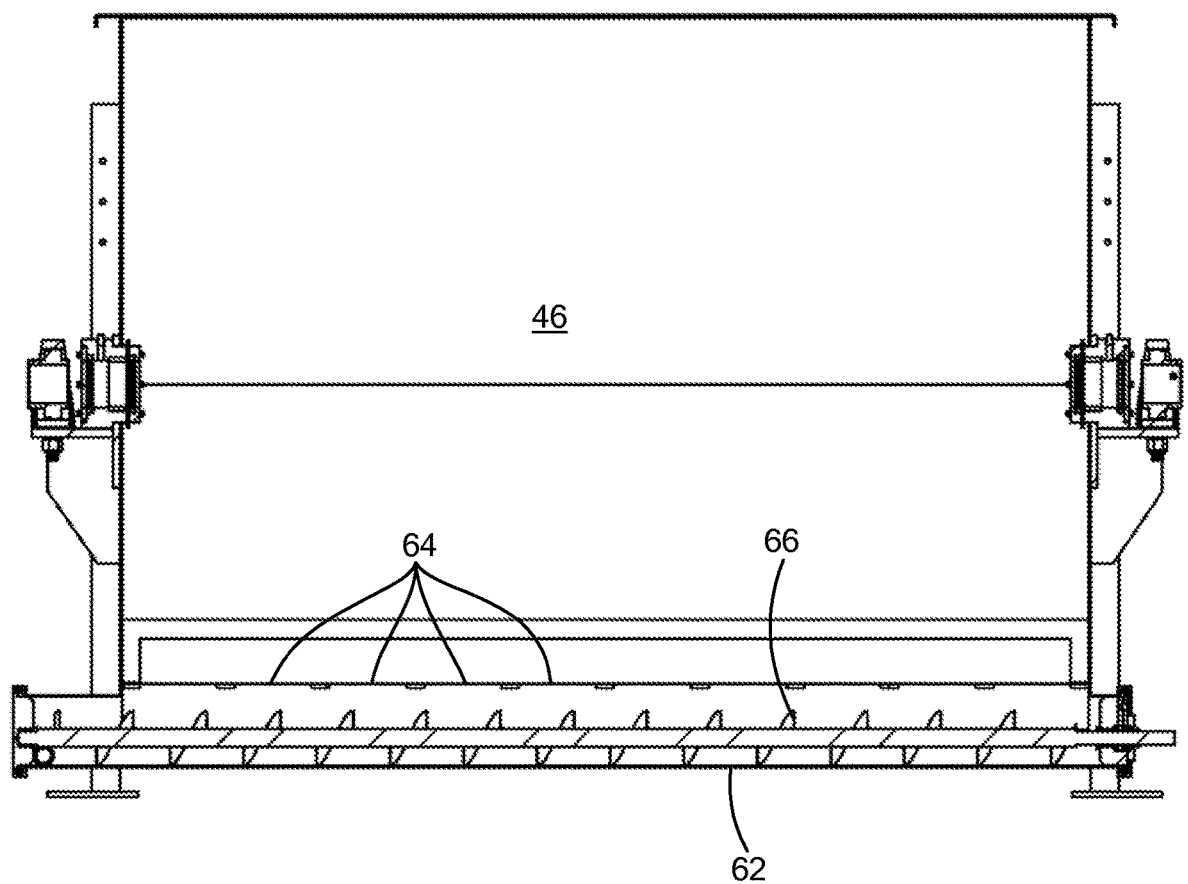
FIG. 9 is cross-sectional front view of the hopper unit of FIG. 6 along line A-A of FIG. 7.
Figure 10:
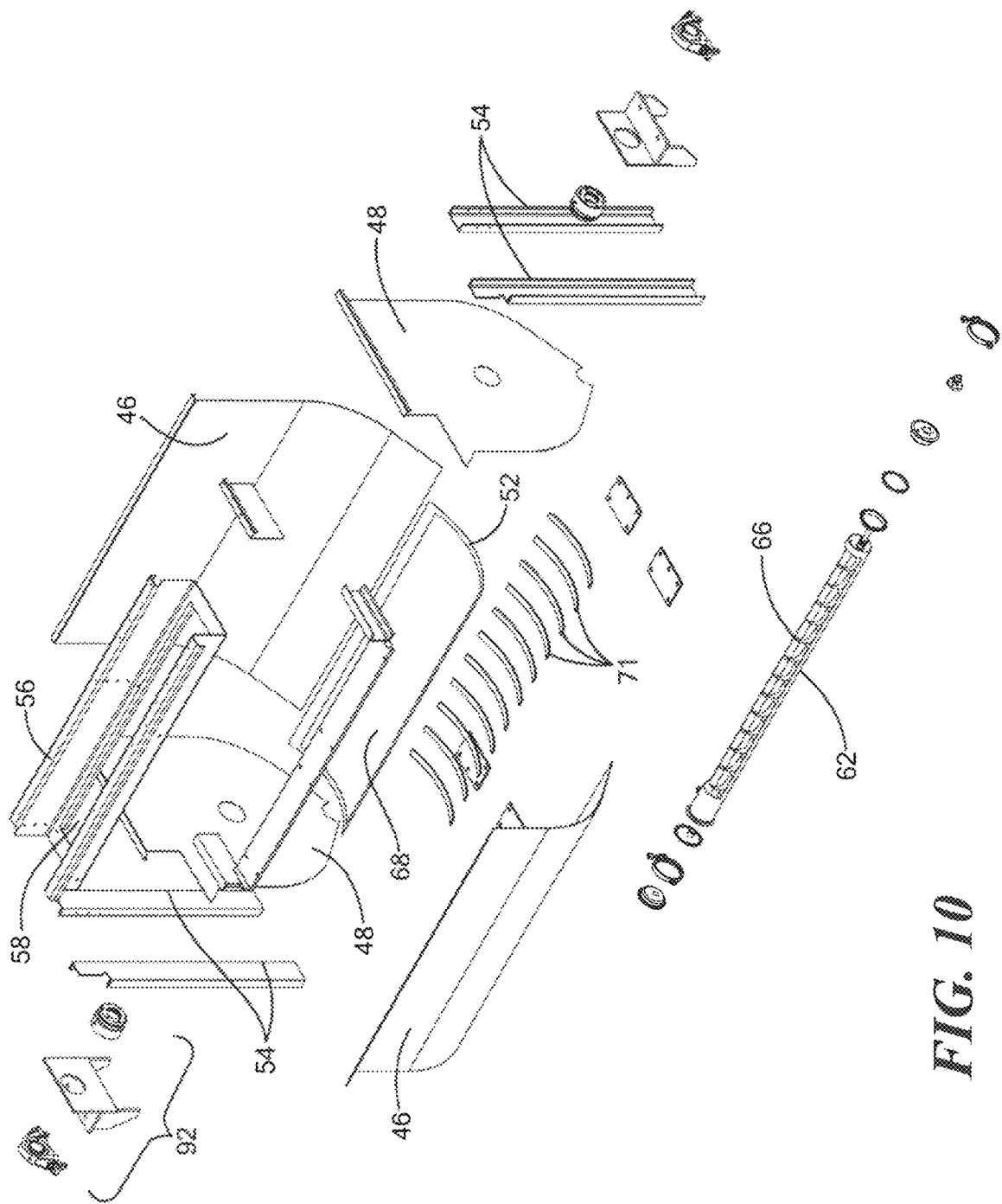
FIG. 10 is an exploded view of the hopper unit of FIG. 6.
Figure 12:
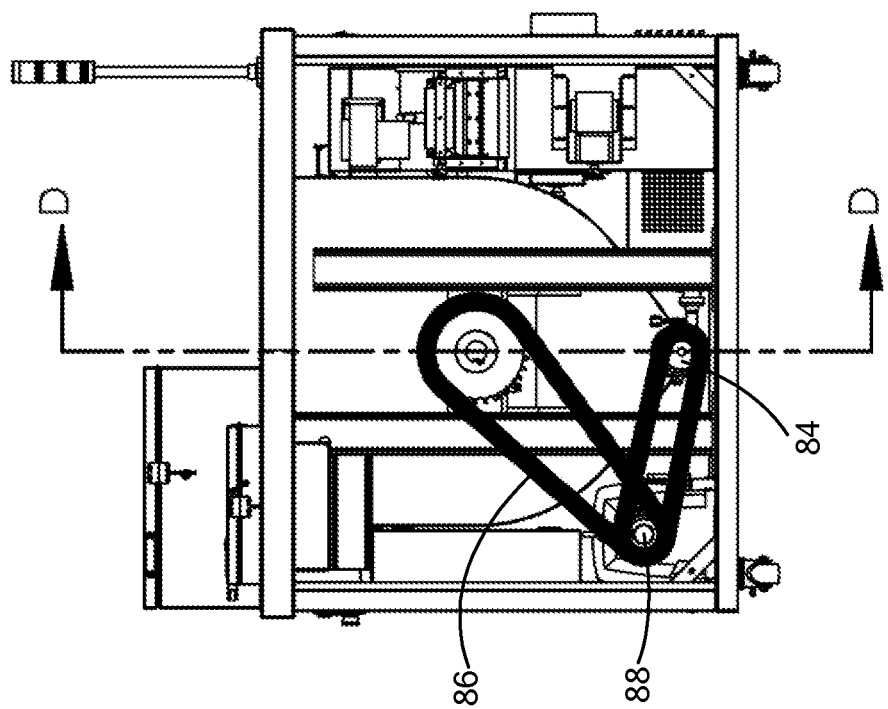
FIG. 12 is a side view of the organic waste digester system of FIG. 2 with a side housing panel removed.
Figure 11:
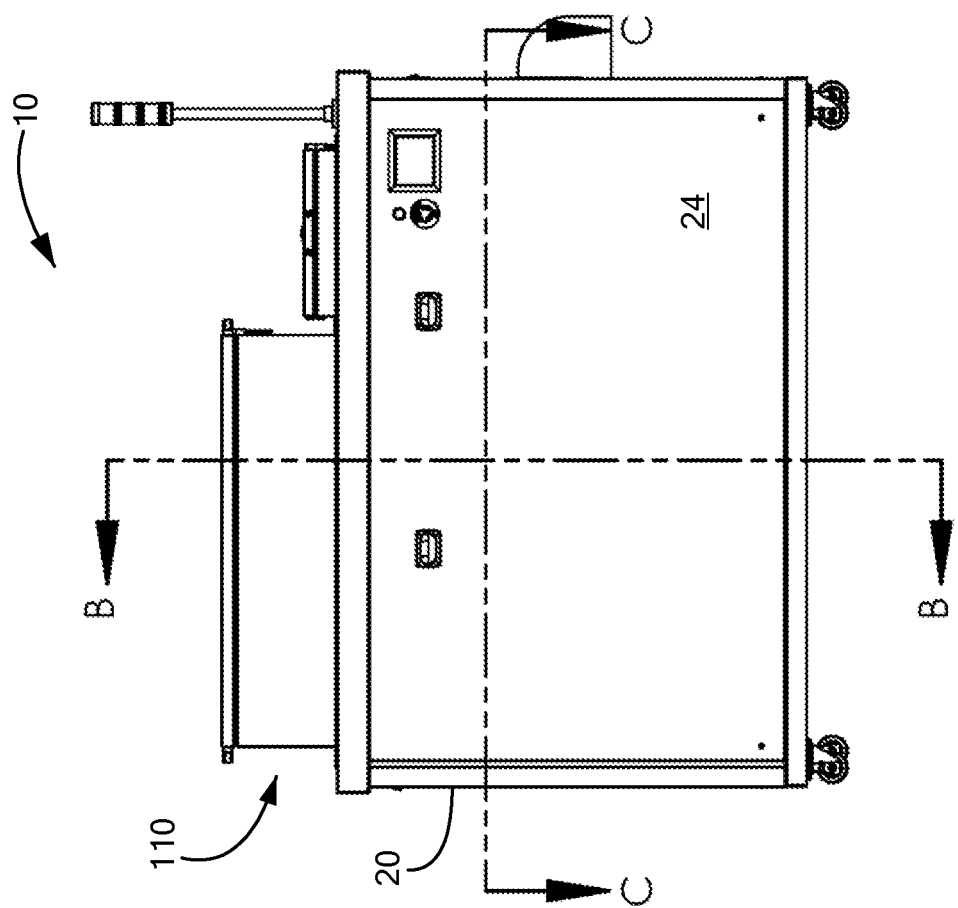
FIG. 11 is a front view of the organic waste digester system of FIG. 2.
Figure 14:
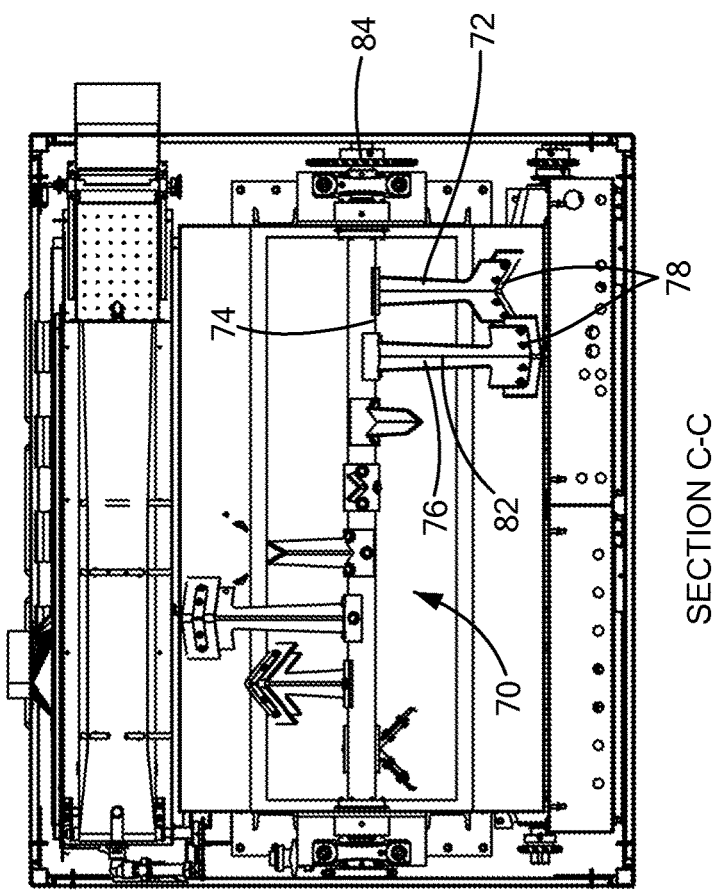
FIG. 14 is a cross-section top view of the organic waste digester system of FIG. 2 along line C-C of FIG. 11.
Figure 13:
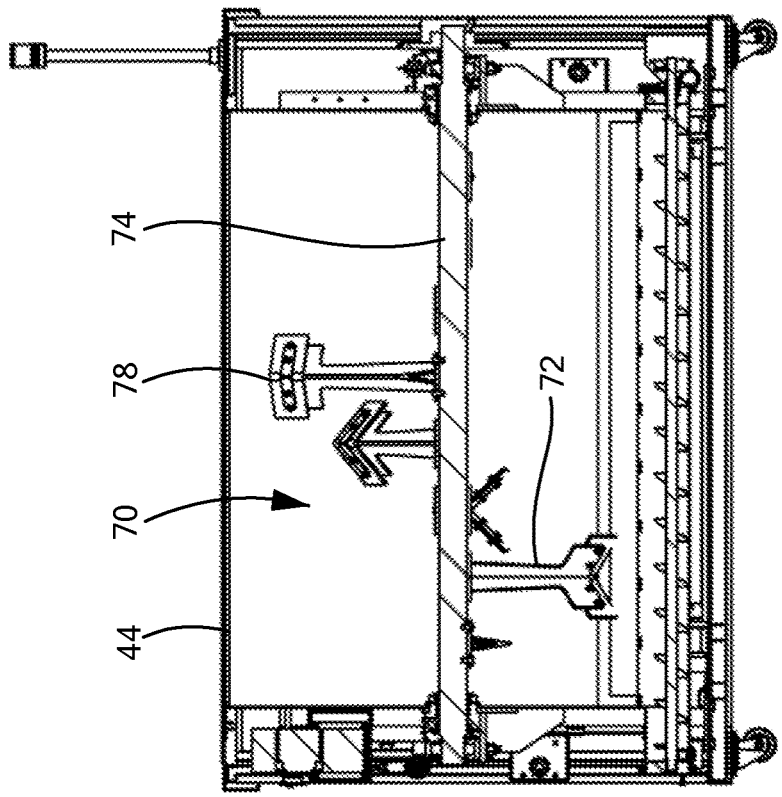
FIG. 13 is a cross-sectional side view of the organic waste digester system of FIG. 2 along line D-D of FIG. 12.
Figure 16:
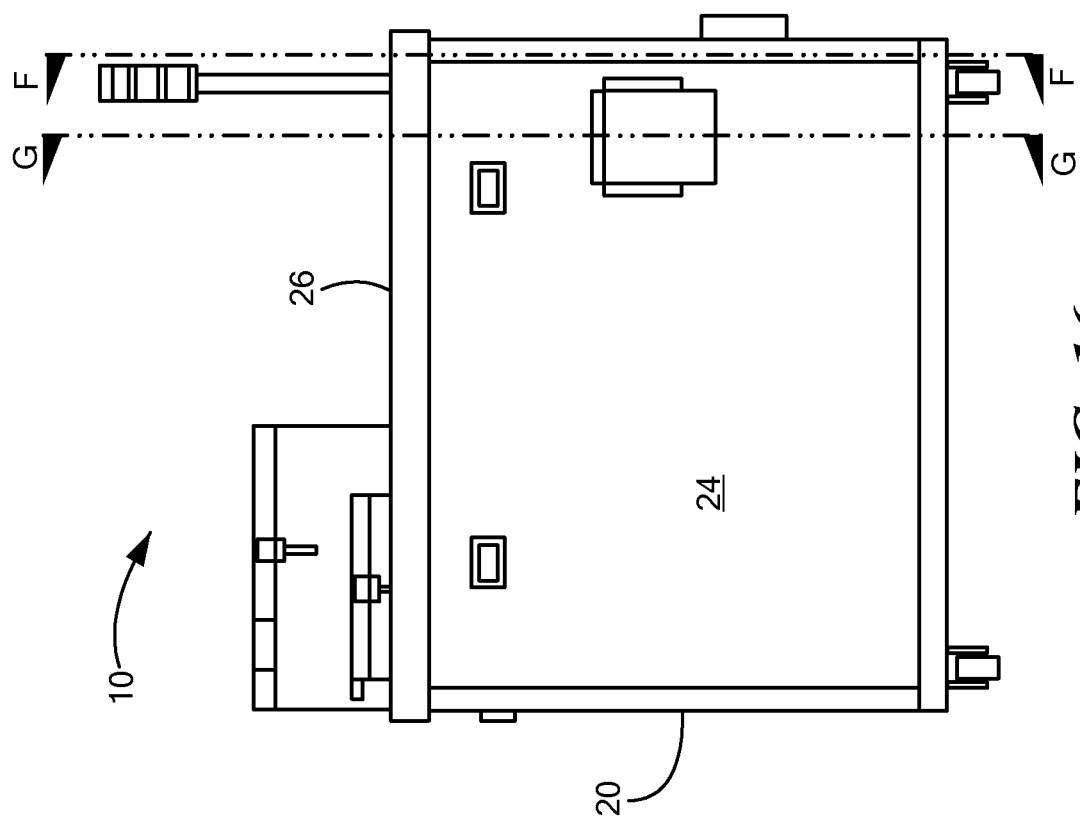
FIG. 16 is a side view of the organic waste digester system of FIG. 2.
Figure 15:
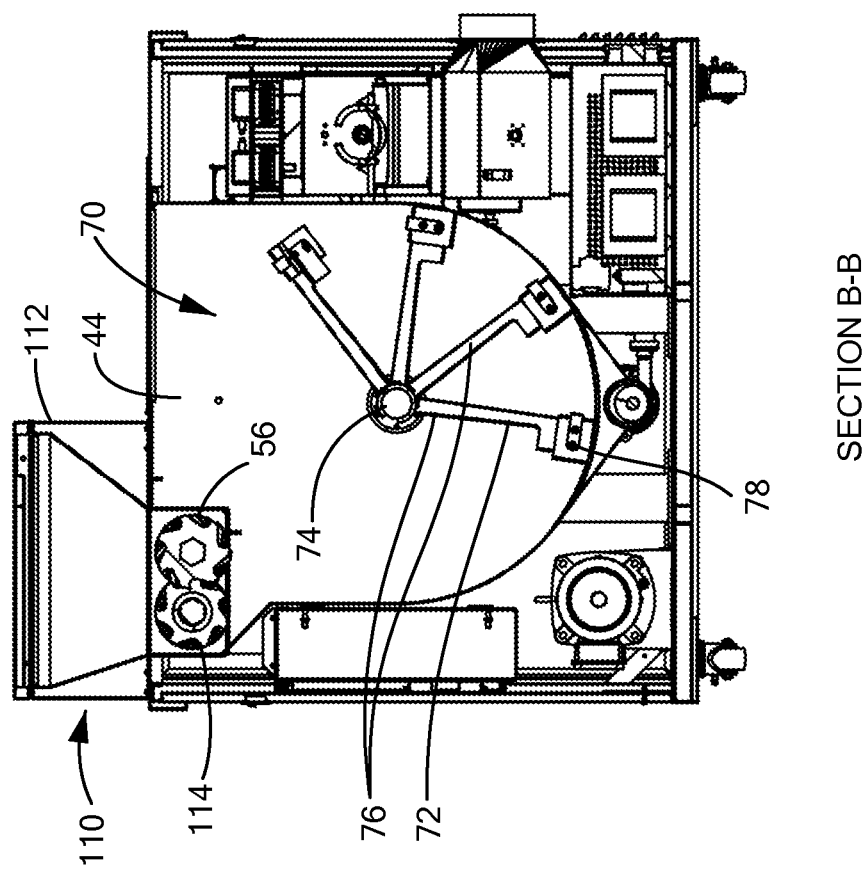
FIG. 15 is a cross-sectional side view of the organic waste digester system of FIG. 2 along line B-B of FIG. 11.
Figure 17:
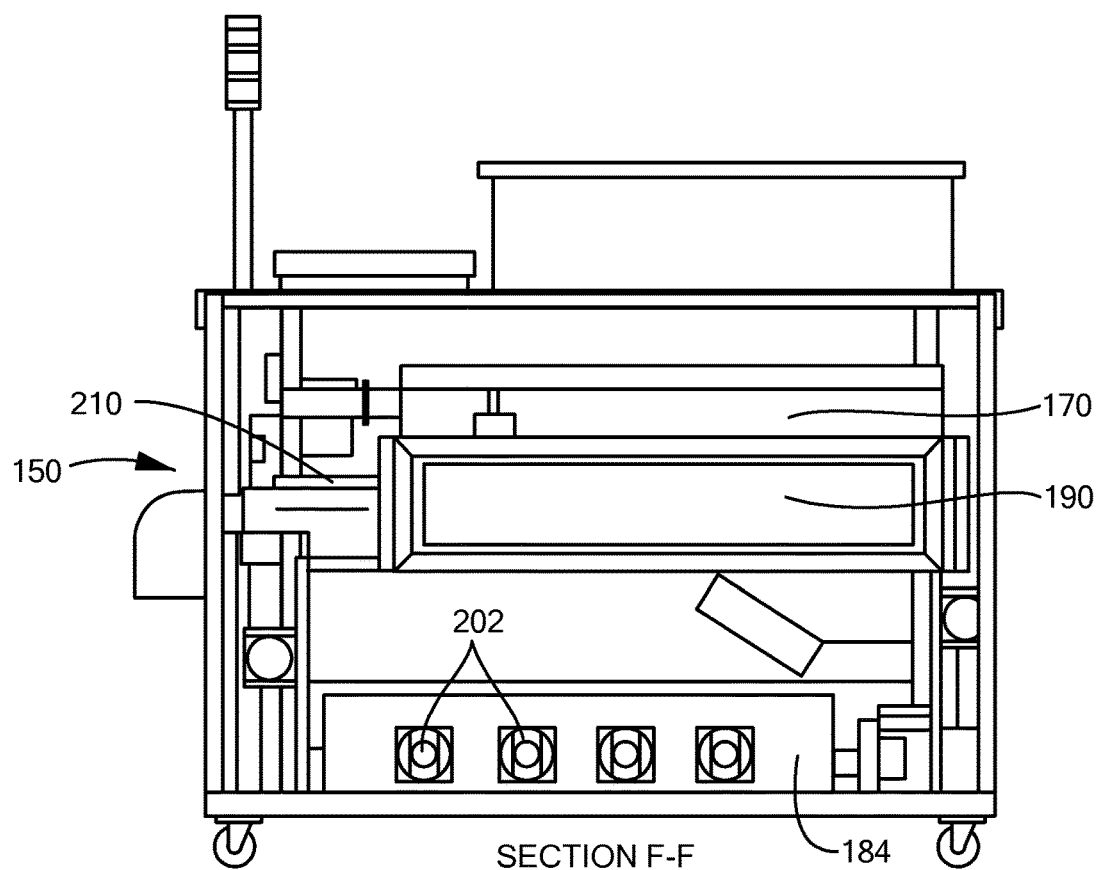
FIG. 17 is a cross-sectional view of the organic waste digester system of FIG. 2 along line F-F of FIG. 16.
Figure 18:
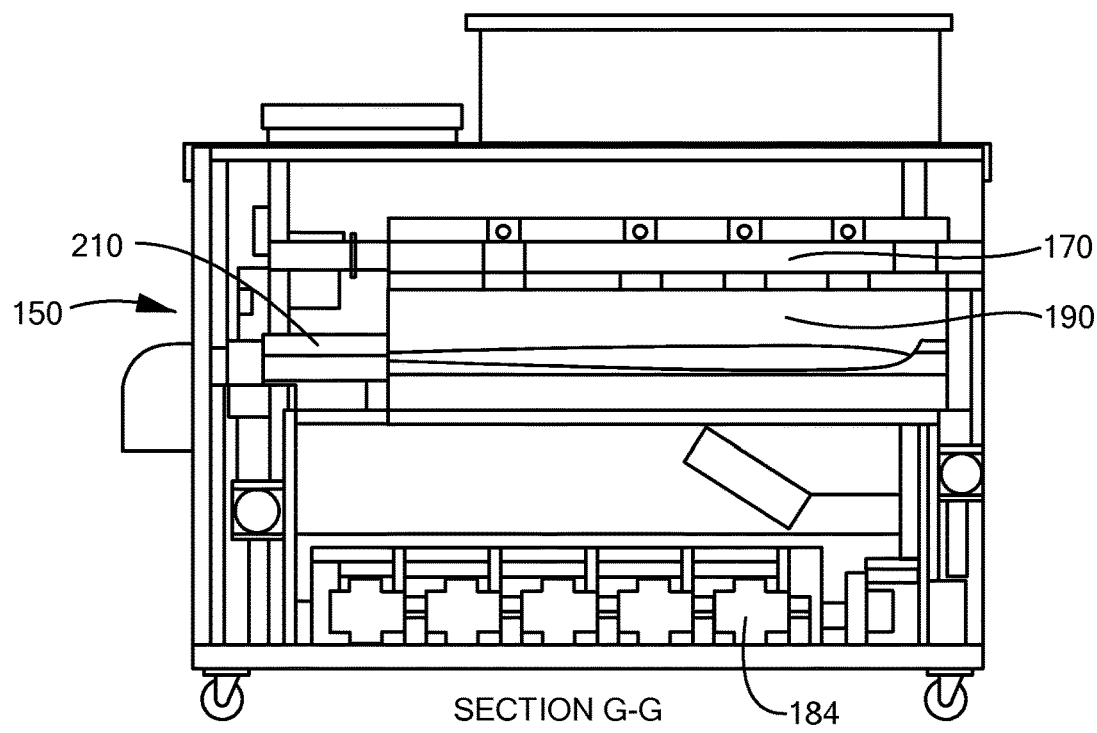
FIG. 18 is a cross-sectional view of the organic waste digester system of FIG. 2 along the line G-G of FIG. 16.
Figure 19:
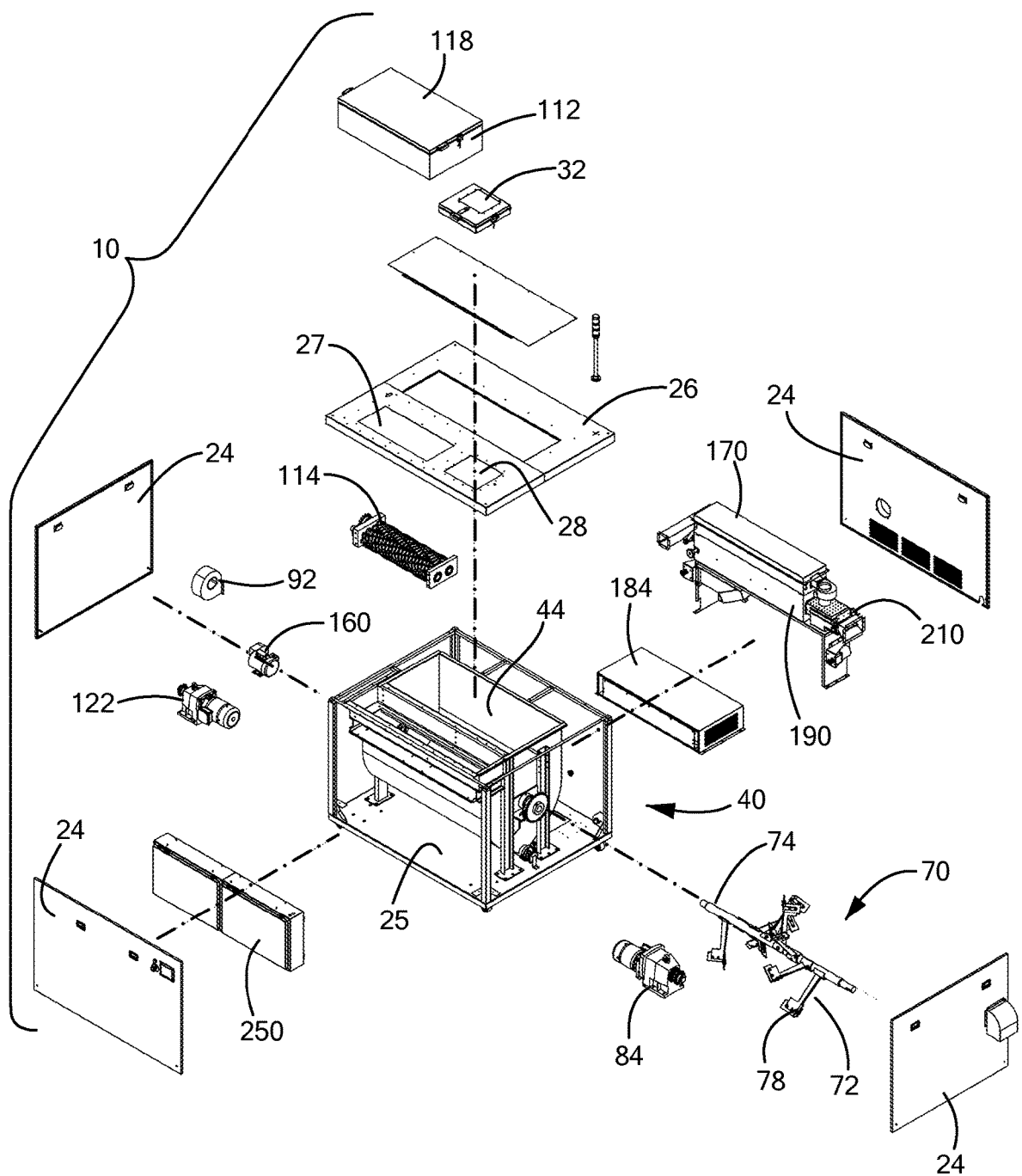
FIG. 19 is an exploded view of the organic waste digester system of FIG. 2.
Figure 20:
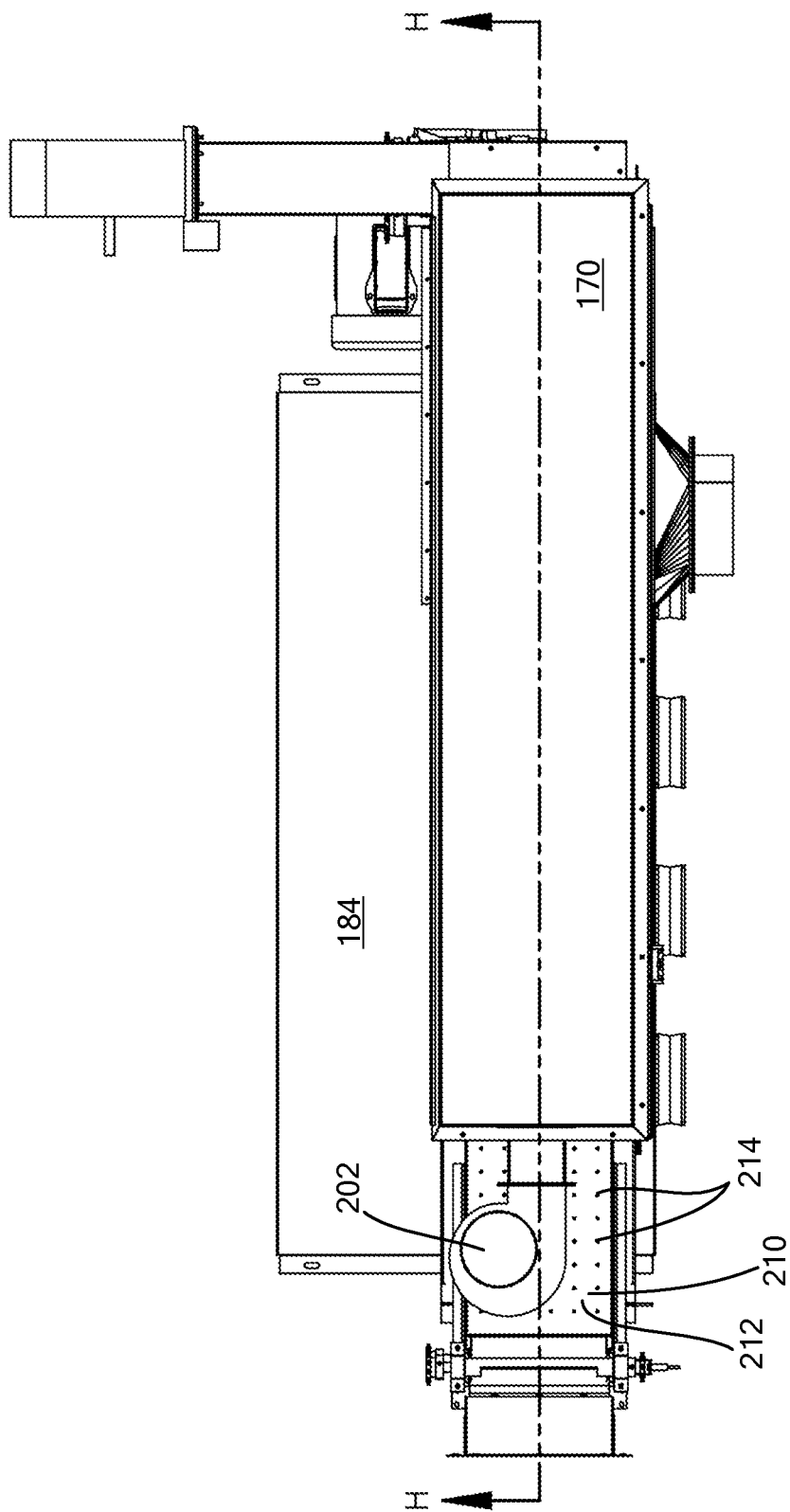
FIG. 20 is a top view of an embodiment of a drying unit in the organic waste digester system of FIG. 2.
Figure 21:
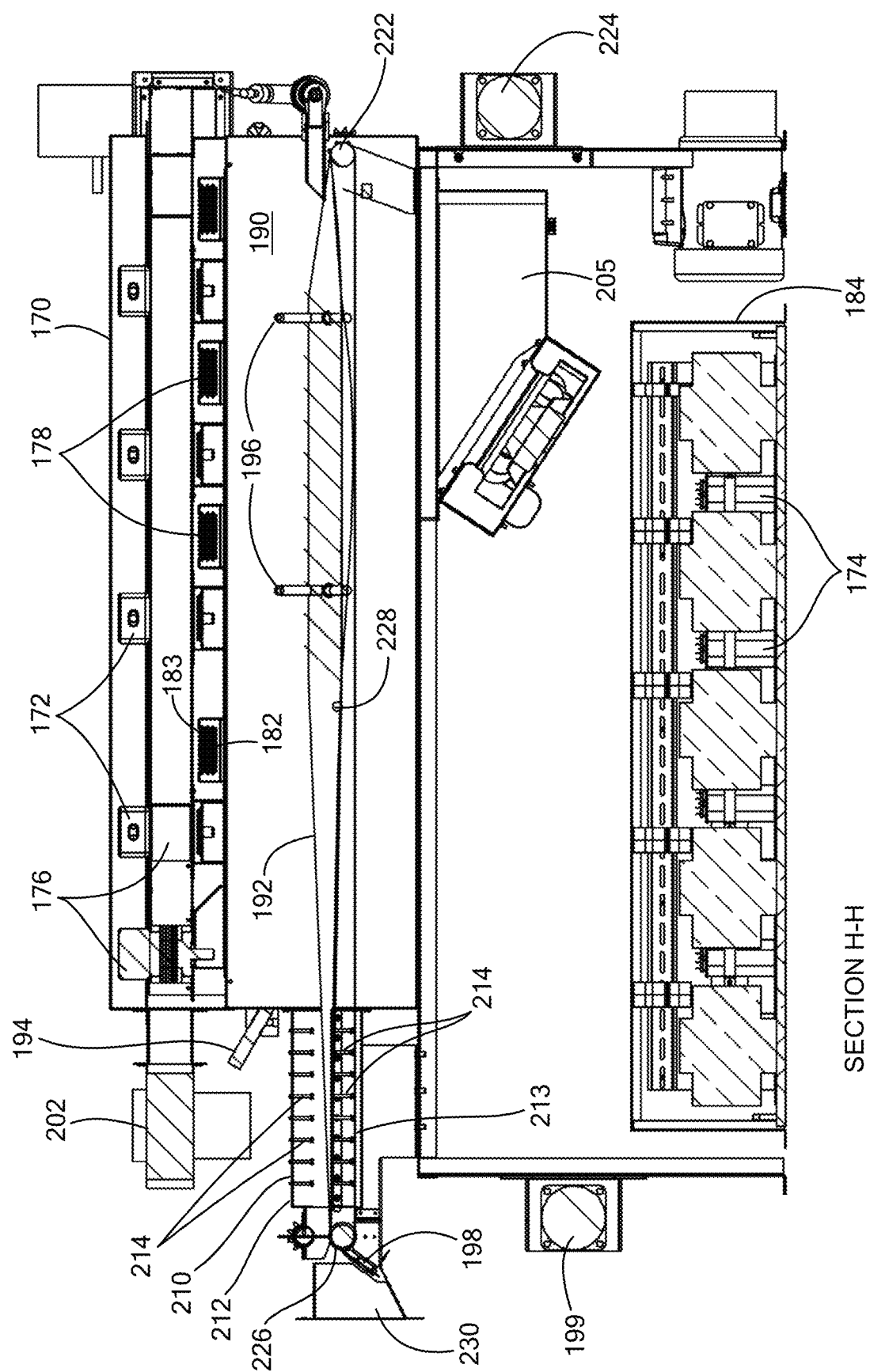
FIG. 21 is a cross-sectional view of the drying unit along line H-H of FIG. 20.
Figure 22:
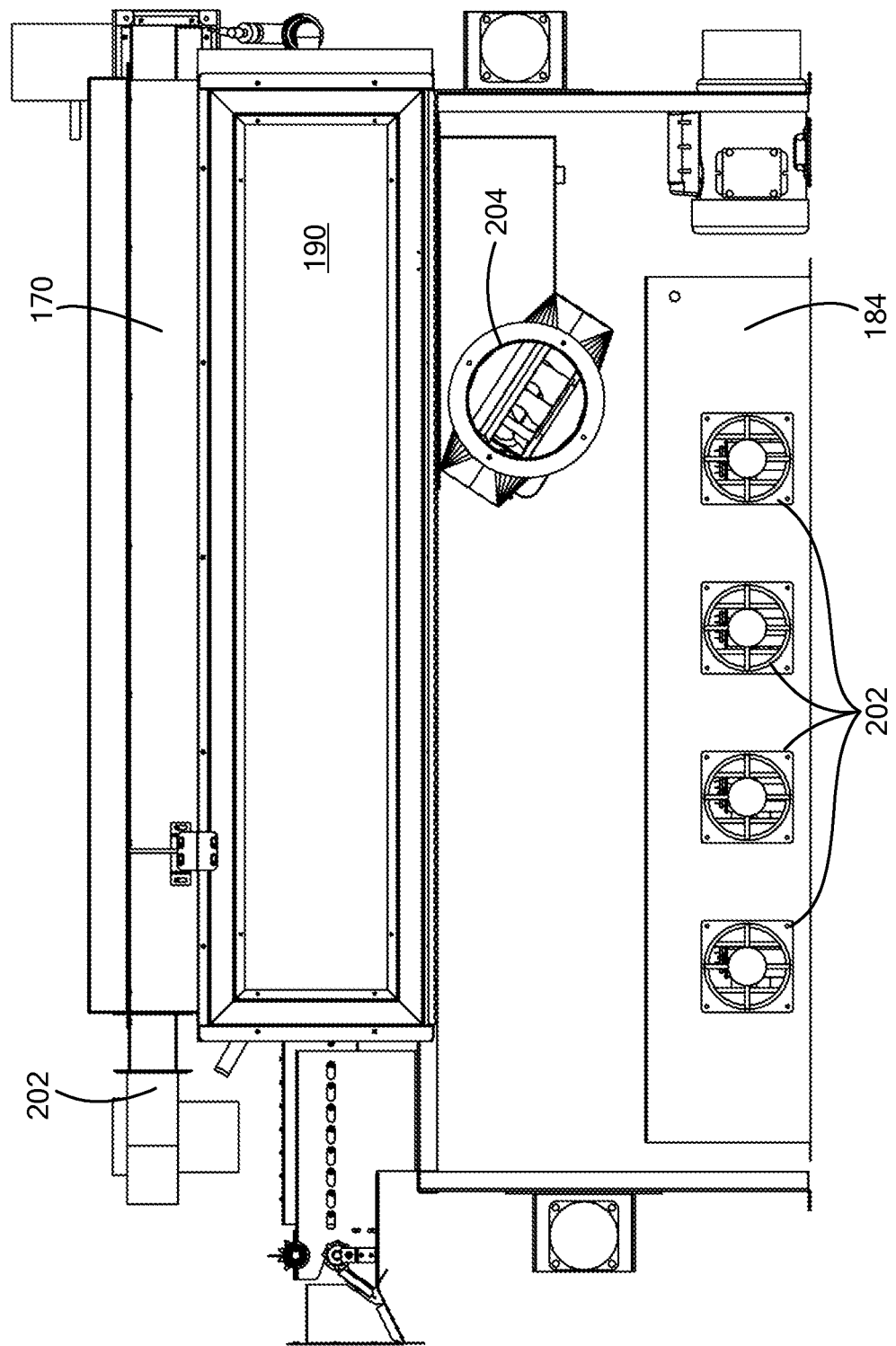
FIG. 22 is an elevation view of the drying unit.
Figure 23:
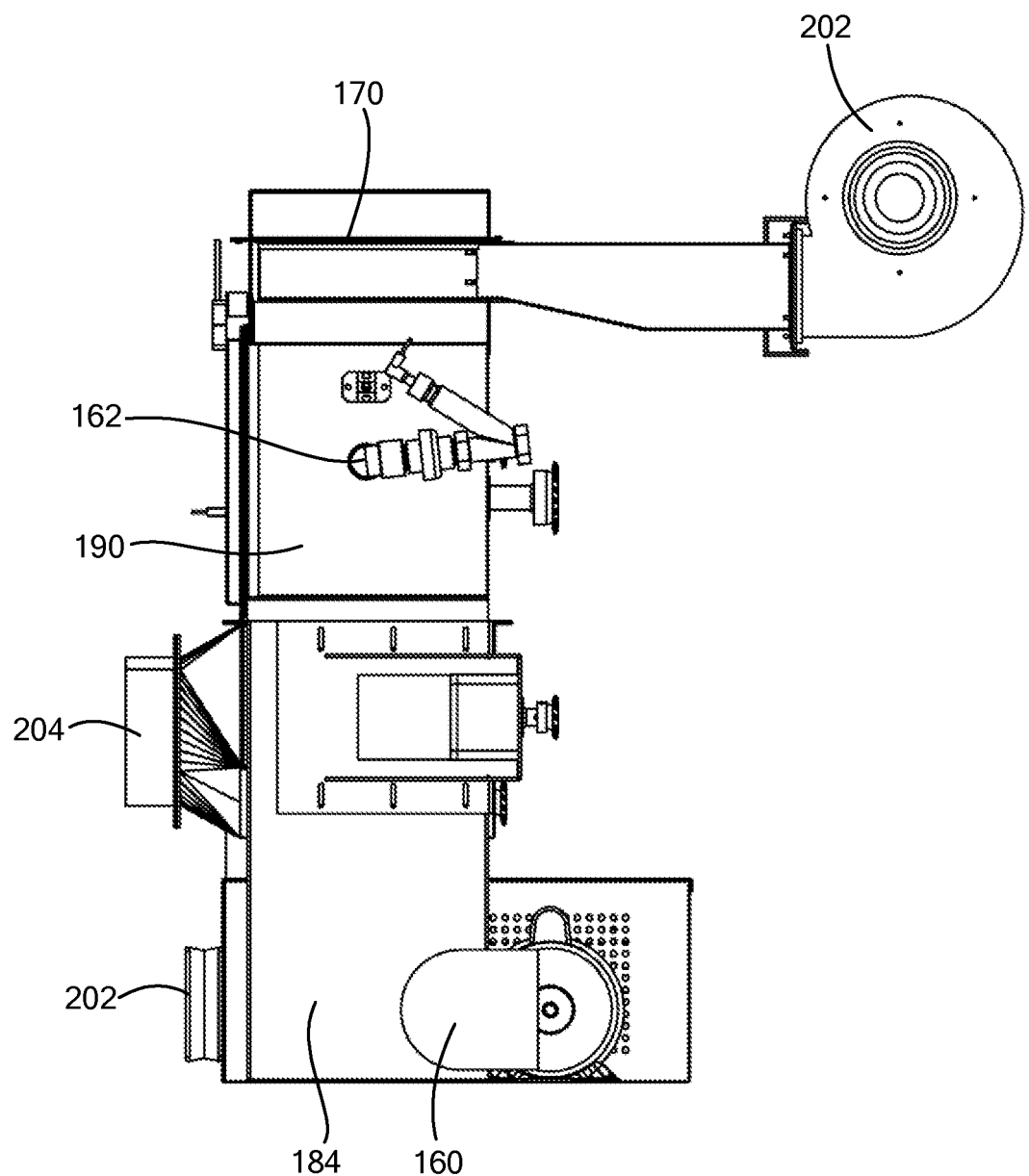
FIG. 23 is a top plan view of the drying unit.

One embodiment of an organic waste digester system 10 is illustrated schematically in FIG. 1. The system includes various components comprising the first stage 12 and second stage 14. In the first stage 12, organic waste 16 is introduced into a hopper unit 40. In the hopper unit, the organic waste is heated and mixed in the presence of a microbe mixture to break down into a liquefied sludge. In the second stage 14, the liquefied sludge is delivered to a drying unit 150 in which it is dried and dehydrated. The dried sludge is discharged out of the system. A control system 250 in communication with the various components controls the operation of the process and the components of the system, as described further below.

Referring to FIGS. 2-5 and 19, the system 10 includes a housing 20 for housing the system formed of various structural framing elements 22 connected to form a frame and covered by side panels 24, lower panel 25, and upper panel 26. An opening 28, covered with a lid 32, in the upper panel of the housing provides access to the hopper unit 40. Organic waste can be deposited directly into the hopper unit 40 through this opening. The system also includes a chopper or grinder unit 110, described further below.

The hopper unit 40 includes a main hopper 42 comprising a hopper bin 44, for example of panels of stainless steel welded or otherwise joined and formed into an appropriate bin shape to receive the waste. In the embodiment shown, the hopper bin includes two side panels 46, two end panels 48, and a bottom panel 52. The bin is supported within the housing 20 by suitable framing elements 54. The main hopper also includes an entrance trough 56 having an open bottom 58 through which the waste is delivered. Waste is deposited into the chopper unit 110, from where it passes through opening 27 into the trough 56 and then into the hopper bin 44.

A microbe mixture that accelerates the breaking down of the food waste is added directly into the main hopper 42, for example, through the opening 28, covered by a lid 32. The microbe mixture typically can be restocked periodically, such as weekly, monthly, quarterly, or annually. Mixing of the organic waste with the microbe mixture begins breaking down and liquefying the organic waste. Suitable microbe mixtures for the liquefaction of organic waste are known and can be used. The microbes can self-regulate their population based on the food supply. In times of high usage and volume, the microbes reproduce and in times of low volume they slow reproduction and go into a dormant state. Users can also view the level of material in the hopper unit through the opening 28 to ensure that the hopper unit is not overfilled.

The hopper unit 40 includes a lower trough 62 along and below the bottom panel 52. See FIGS. 6-10. The bottom panel includes apertures 64 to allow liquid to flow through into the lower trough 62. The lower trough is sloped toward one side of the hopper to allow the sludge (liquefied waste) to flow out into an outlet 65. An auger or other drive mechanism 66 can be placed in the trough to assist movement of the sludge to the outlet. Contaminants such as glass, ceramics, plastic, hard bones, and the like remain in the hopper bin above the bottom panel 52 and can be removed after the system is shut down. In the embodiment shown, the bottom panel 52 is formed with a large opening 68 crossed by with slats 71 spaced apart to form the apertures 64. The apertures can be formed in another other manner, such as by providing slits, slots, or holes in the bottom panel or by placing a screen over a large opening in the bottom panel.

The hopper unit also includes an agitation mechanism 70 to mix the organic waste to help it break down in the presence of the microbe mixture. See also FIGS. 11-15. The agitation mechanism includes a number of auger paddles 72 disposed along an agitator drive shaft 74 in a staggered orientation within the bin 44 of the main hopper 42. In one embodiment, each auger paddle 72 includes a shaft 76 extending orthogonally from the drive shaft to assist the mixing of the food waste. A paddle 78 is disposed at the end of the shaft. The paddle can have any suitable configuration, such as flat or chevron-shaped. Blades 82 can be disposed along sides of the shaft to help the paddles cut through the organic waste. Eight to ten auger paddles are generally sufficient, although any suitable number can be used, depending on the size of the hopper unit.

The agitator drive shaft 74 can be driven in any suitable manner such as by a motor 84 mounted on the frame outside of the hopper bin 44. The motor is in communication with the control system 250, which controls operation of the motor to drive the agitation mechanism 70. The motor is connected via a sprocket and chain or a belt 86 and suitable gearing 88 to the drive shaft. The drive shaft is sealed and supported in a stable manner on the frame, for example, with pillow block bearings 92 and suitable bushings where the drive shaft 74 enters the hopper bin 44 to keep liquids in the hopper bin from leaking out. Any suitable sealing mechanism that allows stable rotation of the agitator drive shaft while preventing leakage can be used.

The main hopper 42 can be heated in any suitable manner. For example, a mat heater can be attached directly to the outer surfaces of the panels of the hopper. The hopper is heated to a temperature range of 80 to 120° F. The hopper bin can include a layer of an insulating material to retain heat.

Referring also to FIGS. 4-5, 15, and 19, the chopper unit 110 initially chops all the organic material, including meat and small bones, that is deposited into the hopper unit, thereby increasing the surface area of the organic waste, which speeds up decomposition. The chopper unit includes a hopper 112 mounted above the opening 27 in the surface 26 of the housing 20, and a chopping blade mechanism 114 that fits within the trough 56. An opening 116 covered with a lid 118 provides access to the hopper 112. In one embodiment, the chopping blade mechanism 114 includes a pair of meshing rotary cutters. In another embodiment, the chopping blade mechanism can include a rotary chopper knife formed of a number of individual, stacked rotary blade elements aligned and radially spaced equally about a shaft. A chopper motor 122 spins the blades on the shaft, thereby chopping any organic waste in the chopper hopper into smaller pieces. The chopper motor 122 is also in communication with the control system 250. The organic waste passing through the chopper unit is discharged through the trough directly into the main hopper. In another embodiment, the chopper unit can be eliminated, if desired, and organic waste can be deposited directly into the hopper bin without an initial chopping.

From the hopper unit, the sludge is pumped by a pump 160 through suitable hosing or conduits (not shown for clarity) to an inlet 162 of the drying unit 150 of the second stage to effect drying and dehydrating. See FIGS. 16-23. Suitable fittings to which conduits are attached can be provided at the outlet 65 of the hopper unit and the inlet 162 of the drying unit. A level sensor in the hopper unit can be used to determine when an appropriate amount of sludge is available and to send a signal to the control system, which then engages the pump 160. The control system 250 then turns on the drying unit to affect the drying and dehydration. The drying unit 150 can be located within the housing 20, as shown, or can be external to the housing, for example, adjacent to the housing or on top of the housing. Optionally, a storage vessel 159 (see FIG. 1) can be provided to store the sludge (the liquefied waste) as it is removed from the hopper before transfer to the drying unit.

The drying unit 150 heats the liquefied sludge to a temperature within a range of 215 to 300° F., which is sufficient to effectively kill pathogens, bacteria, and seeds. In one embodiment, a drying unit 150 uses microwave energy to effect the drying of the sludge. Referring to FIGS. 16-23, the drying unit includes a microwave generation chamber 170 for supporting and housing one or more microwave units 172, in communication with the control system 250, a microwave application chamber 190 through which the sludge is transported, for example, on a conveyor belt 192, while being heated by application of the microwave energy, and a microwave suppression chamber 210 at the outlet of the application chamber. Each microwave unit 172 includes a high voltage transformer 174 and associated magnetron tube 176 and waveguide 178. The waveguides are disposed to direct microwave energy through a wall 182, such as a floor in the embodiment shown, into the microwave application chamber 190. In the embodiment shown, the microwave generation chamber 170 housing the magnetron tubes and waveguides is disposed above the microwave application chamber 190, while the associated transformers are housed in a separate power plant enclosure 184 below the application chamber for better control of the high heat generated. However, other configurations can be used if desired, such as placing the microwave application enclosure alongside or above the microwave generation chamber, and/or placing the transformers within the same chamber as the magnetron tubes and waveguides.

The microwave suppression chamber 210 at the outlet of the microwave application chamber prevents microwave radiation from leaking out of the application chamber. The suppression chamber includes an upper wall 212 and lower wall 213 supporting an appropriate number of suppression pins 214 extending into the chamber. The pins are of any suitable number, size, and spacing depending on the frequency of the microwaves generated to suppress the microwave radiation. Other suppression configurations can be used. The conveyor belt extends through the suppression chamber to transport the dried sludge so that it can be discharged out of the drying unit. The conveyor belt returns below the lower wall 213 and through an opening between the suppression chamber and the application chamber.

One or more cooling fans or blowers 202 are disposed to draw cool air into the drying unit to cool the microwave generation enclosure, the power plant enclosure, and the microwave suppression chamber. The fans can be disposed in any suitable wall or walls, such as a side wall or ceiling. The ambient air within the microwave generation chamber is heated as a byproduct of cooling the magnetrons. The heated air can be introduced into the microwave application chamber, for example, through the microwave waveguides. The waveguides can include a grate or another suitable opening 183 for the heated ambient air to pass through. An exhaust fan 204 is also provided to exhaust air from the drying unit. Any suitable number of cooling fans and exhaust fans can be used.

In one example, the microwave drying unit 150 operates at 2400 MHz frequency, 220 V, 3 phase AC current at 9.6 kilowatts total power. Any suitable number of microwave units can be used, depending on, for example, the application and the amount of material to be digested. In one embodiment, nine microwave units are used. Similarly, any suitable convective and/or forced cooling arrangement of the magnetrons can be used.

The sludge to be dried passes through the microwave application chamber 190 and suppression chamber 210 in any suitable manner. For example, a conveyor belt 192 can be provided that travels the length of the application chamber. The sludge enters the application chamber through an inlet 162 and is deposited onto the conveyor belt. The inlet can include, for example, a tube fitting connected to a conduit from the pump 160. The sludge passes along, for example, beneath, the row of waveguides 178 of the microwave units, which directs microwave energy and heated air onto the sludge. The sludge is thereby heated by radiative heating and convective heating to effect the drying.

A temperature sensor 194 (see FIG. 21) is disposed in the application chamber near the output end. In one example, an infrared temperature sensor is used to monitor the temperature of the sludge as it exits the conveyor belt. The temperature of the sludge is roughly analogous to the final moisture content of the sludge. The particular correlation depends on the type of organic waste that is introduced into the system, and can be readily determined by testing. For example, in one example, a temperature of at least 340° F. indicates a moisture content of no more than 10%. The type of organic waste is generally consistent at a particular location, and thus once a correlation between temperature and moisture content has been determined for that location, the temperature can serve as a suitable determination of the moisture content. For most applications, the moisture content of the sludge as it is discharged from the application chamber is in the range of 10 to 13%. It will be appreciated that the moisture content can vary, for example, from a low of 1%, 2%, 3%, 4%, 5%, 6%, 7%, 8%, 9%, or 10% to a high of 13%, 14%, 15%, 20% or 25%. The temperature sensor is in communication with the control system, which can control each of the microwave units individually to provide a desired amount of heating. For example, the control system can operate the microwave units closest to the inlet end of the application chamber at a higher power to provide a greater amount of heating to the sludge. The microwave units nearer the outlet end can be operated as needed, depending on the moisture content of the sludge.

The conveyor belt 192 is formed of a soft material that is able to be formed with a cupped shape in transverse cross section at and near the inlet end of the application chamber. The cupped shaped is formed by side guards 196 (shown schematically in FIG. 21). The entering sludge still has a high moisture content, and the cupped shape of the conveyor belt retains the water within the longitudinal edges of the belt while the sludge is heated and the water evaporates. The belt is also solid, so that liquids and solid particulates cannot fall through. As the sludge dries and is transported toward the outlet end of the application chamber, the conveyor belt takes on a flat configuration, such that it is substantially flat at the discharge end. The flat configuration of the belt at the discharge end allows the sludge to be more readily removed from the conveyor belt, for example, with a blade, knife, or scraper 198 at the discharge end the belt. In one embodiment, a cutting blade or knife 198, operable by a motor 199 in communication with the control system 250, is provided at the discharge end of the belt to cut the sludge into blocks or segments.

The conveyor belt includes any suitable driving mechanism, such as a drive roller 222, motor 224, a return roller 226, and tensioning mechanism. An idler roller 228 can be provided to flatten the belt. A suitable material for the belt is a silicone material, which can be repeatedly deformed into a cupped configuration at the entrance and then flattened at the discharge end as the belt cycles through the application chamber.

At the outlet end of the suppression chamber, the conveyor belt deposits the sludge into an outlet duct 230. The dried sludge 300 can be collected and transported to a collection device.

In some embodiments, the outlet duct can be in communication with a vacuum source to assist in pulling the dried sludge off the conveyor belt and into and through the outlet duct. Process air in the application chamber is also vented through the exhaust duct.

In a further embodiment, exhaust products from the application chamber, containing dry particles and moist process air, can be conveyed via a vacuum system into a collection canister 205. The process air can be filtered to remove any suspended particles and exhausted to ambient through a vacuum blower. In a still further embodiment, the process air can be transmitted to an air dryer or dehumidifier that removes moisture before discharging the dehumidified air to ambient.

The control system 250 can be located in a panel 260 that also houses the electrical wiring, fuses, circuit breakers, and the like. In one embodiment, the control system 250 is a programmable logic controller. The control system includes a display 252 with an operator input device such as a keypad and a display screen for outputting messages. The control system can be programmed to indicate any stoppages, failures, errors, or maintenance needs. A cut-off switch can be provided so that, when the main hopper lid 32, the chopper lid 118, or an access panel 119 is opened during operation, the unit shuts off. A visual indicator light or lights 254 can be provided to illuminate when the main hopper lid and/or the chopper lid are open. In one embodiment, lights are provided on a pole 256 elevated above the housing so that they are readily visible. An emergency stop button 258 can be located in a relatively accessible location on the outside of the unit.

The present organic waste digester system is able to maintain optimum levels of aeration, moisture and temperature during the digesting process. The system is self-contained and organic waste can be continually added. The cycle time from initial input of organic waste to the discharge of a compostable material can be as little as 3.5 hours. The system does not require the addition of water and does not need to be plumbed into an existing water supply. The organic waste digester system does not discharge gray water. No liquid waste is produced during the evaporation process.

It will be appreciated that the various features of the embodiments described herein can be combined in a variety of ways. For example, a feature described in conjunction with one embodiment may be included in another embodiment even if not explicitly described in conjunction with that embodiment.

The present invention has been described with reference to the preferred embodiments. It is to be understood that the invention is not limited to the exact details of construction, operation, exact materials or embodiments shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

What is claimed is:

1. An organic waste digester system, comprising:
    a hopper unit, the hopper unit including a bin to receive organic waste, an agitation mechanism to mix the organic waste, a heater to heat the organic waste within the bin, and an outlet through which liquefied organic waste is discharged;
    a drying unit downstream of the hopper unit to receive and dry the liquefied organic waste from the hopper unit, the drying unit comprising:
        a microwave drying unit comprising a microwave generation chamber and a microwave application chamber, wherein the microwave generation chamber includes a plurality of microwave units, each microwave unit including a waveguide disposed to direct microwave radiation into the microwave application chamber, and
        a conveyor disposed to travel through the microwave application chamber, the conveyor configured to receive the liquefied organic waste from the hopper unit.

2. The system of claim 1, further comprising one or more cooling fans in the microwave generation chamber to cool the microwave units.

3. The system of claim 1, further comprising one or more openings between the microwave generation chamber and the microwave application chamber to direct heated air into the microwave application chamber.

4. The system of claim 3, wherein the one or more openings are disposed through an associated wave guide.

5. The system of claim 1, further comprising a microwave suppression chamber disposed at an outlet of the microwave application chamber.

6. The system of claim 5, wherein the conveyor is disposed to travel through the microwave suppression chamber.

7. The system of claim 1, wherein the conveyor comprises a conveyor belt having a cupped shape in transverse cross-section at an inlet end of the microwave drying unit and a flat configuration at an outlet end of the microwave drying unit.

8. The system of claim 7, further comprising an outlet duct disposed at the outlet end of the microwave drying unit to receive organic waste.

9. The system of claim 8, further comprising a blade to scrape organic waste off the conveyor into the outlet duct.

10. The system of claim 8, further comprising a vacuum source disposed to exert a negative pressure at the outlet duct.

11. The system of claim 7, further comprising an exhaust duct disposed at the outlet end of the microwave drying unit configured to remove exhaust products from the microwave drying unit.

12. The system of claim 11, further comprising a collection canister on the exhaust duct to receive dry particles.

13. The system of claim 11, further comprising a filter on the exhaust duct to remove suspended particles.

14. The system of claim 11, further comprising a dehumidifier on the exhaust duct to remove moisture from process air.

15. The system of claim 1, further comprising a control system in communication with the hopper unit and the drying unit.

16. The system of claim 15, further comprising a temperature sensor disposed in the microwave application chamber, the control system in communication with the temperature sensor and the microwave units, and operative to control the microwave units to provide a determined temperature within the microwave application chamber.

17. The system of claim 1, wherein the hopper unit further includes a chopper unit comprising a chopper hopper and a chopping mechanism disposed at an entrance to the bin of the hopper unit.

18. The system of claim 1, wherein the heater is operative to heat the bin to a temperature range of 80 to 120° F.

19. The system of claim 1, further comprising a microbe mixture to accelerate breakdown of the organic waste within the bin.

\* \* \* \* \*